United States Patent
Song et al.

(10) Patent No.: US 9,994,869 B2
(45) Date of Patent: Jun. 12, 2018

(54) METHOD FOR PRODUCING ISOPRENE USING RECOMBINANT HALOPHILIC METHANOTROPH

(71) Applicants: SK Innovation Co., Ltd., Seoul (KR); San Diego State University Research Foundation, San Diego, CA (US)

(72) Inventors: JaeYang Song, Daejeon (KR); Kwang Kuk Cho, Daejeon (KR); Ki Sung Lee, Daejeon (KR); Yeon Hwa La, Daejeon (KR); Marina Kalyuzhnaya, San Diego, CA (US)

(73) Assignees: SK Innovation Co., Ltd., Seoul (KR); San Diego State University Research Foundation, San Diego, CA (US)

( * ) Notice: Subject to any disclaimer, the term of this patent is extended or adjusted under 35 U.S.C. 154(b) by 0 days. days.

(21) Appl. No.: 15/392,408

(22) Filed: Dec. 28, 2016

(65) Prior Publication Data

US 2017/0211100 A1    Jul. 27, 2017

(30) Foreign Application Priority Data

Jan. 26, 2016    (KR) ........................ 10-2016-0009372

(51) Int. Cl.
*C12N 1/20* (2006.01)
*C12P 5/00* (2006.01)
*C12N 9/88* (2006.01)
*C12N 15/52* (2006.01)

(52) U.S. Cl.
CPC ................ *C12P 5/007* (2013.01); *C12N 1/20* (2013.01); *C12N 9/88* (2013.01); *C12N 15/52* (2013.01);

(Continued)

(58) Field of Classification Search
None
See application file for complete search history.

(56) References Cited

U.S. PATENT DOCUMENTS 5,849,970 A    12/1998    Fall et al.
2015/0225743 A1    8/2015    Donaldson et al.
(Continued)

FOREIGN PATENT DOCUMENTS

| KR | 1020150160066 A | 9/2015 |
| WO | 2014089436 A1 | 6/2014 |
| WO | 2014138419 A1 | 9/2014 |

OTHER PUBLICATIONS

Guo et al., "Protein tolerance to random amino acid change", Proceedings of the National Academy of Sciences USA, vol. 101, No. 25, pp. 9205-9210, 2004.*

(Continued)

*Primary Examiner* — Richard C Ekstrom
(74) *Attorney, Agent, or Firm* — The Webb Law Firm

(57) ABSTRACT

The present invention relates to a recombinant methanotroph having an ability to produce isoprene and a method for producing isoprene using the same, and more particularly to a recombinant methanotroph having an ability to produce isoprene wherein a gene encoding an isoprene synthase having a homology of at least 70% to the amino acid sequence of *Ipomoea batatas* isoprene synthase is introduced into the recombinant methanotroph, and a method for producing isoprene using the recombinant methanotroph. The use of a recombinant methanotroph according to the present invention enables isoprene to be produced in high yield by using methane gas or methanol which is obtained from waste such as natural gas, biomass, municipal waste or the like as a carbon source.

5 Claims, 2 Drawing Sheets

(52) U.S. Cl.
CPC ..... *C12Y 402/03027* (2013.01); *Y02E 50/343* (2013.01)

(56) References Cited

U.S. PATENT DOCUMENTS

| | | |
|---|---|---|
| 2015/0315599 A1 | 11/2015 | Shelly et al. |
| 2015/0337338 A1* | 11/2015 | Furutani ................. C12N 9/88 435/167 |
| 2016/0017374 A1 | 1/2016 | Leonard et al. |
| 2017/0211056 A1* | 7/2017 | Oja ......................... C12P 5/026 |

OTHER PUBLICATIONS

Julsing et al., "Functional analysis of genes involved in the biosynthesis of isoprene in Bacillus subtilis."; Applied Microbiology and Biotechnology; 2007; pp. 1377-1384; vol. 75.

Kuzma et al., "Bacteria Produce the Volatile Hydrocarbon-Isoprene."; Current Microbiology; 1995; pp. 97-103; vol. 30.

Ojala et al., "Genetic Systems for Moderately Halo (Alkali)philic Bacteria of the Genus *Methylomicrobium*."; Methods in Enzymology; 2011; pp. 99-118; vol. 495.

Puri et al., "Gentle Tools for the Industrially Promising Methanotroph Methylomicrobium buryatense."; Applied and Environmental Microbiology, 2015; pp. 1775-1781; vol. 81:5.

Silver et al. ,"Enzymatic Synthesis of Isoprene from Dimethylallyl Diphosphate in Aspen Leaf Extracts"; Plant Physiology; 1991; pp. 1588-1591; vol. 97.

Silver et al., "Characterization of Aspen Isoprene Synthase, an Enzyme Responsible for Leaf Isoprene Emission to the Atmosphere"; The Journal of Biological Chemistry; 1995; pp. 13010-13016; vol. 270:22.

Wagner et al., "Three Distinct Phases of Isoprene Formation during Growth and Sporulation of bacillus subtilis."; Journal of Bacteriology; 1999; pp. 4700-4703; vol. 181:15.

Weissermel et al., Industrial Organic Chemistry; 2003; pp. 117-122; Wiley-VHC GmbH & Co. KGaA; Germany.

Wilkins et al., "Volatile Metabolites from Actinomycetes."; Chemosphere; 1996; pp. 1427-1434; vol. 32:7.

* cited by examiner

SEQUENCE LISTING

<160> NUMBER OF SEQ ID NOS: 6

<210> SEQ ID NO 1
<211> LENGTH: 541
<212> TYPE: PRT

-continued

<213> ORGANISM: Ipomoea batatas

<400> SEQUENCE: 1

```
Met Thr Ala Arg Arg Ser Ala Asn Tyr Gln Pro Ser Trp Ser Tyr
 1               5                  10                  15

Asp Glu Tyr Leu Val Asp Thr Thr Asn Asp Ser Lys Leu Arg Ile
             20                  25                  30

Gln Glu Asp Ala Arg Lys Lys Leu Glu Glu Val Arg Asn Val Leu
         35                  40                  45

Glu Asp Gly Lys Leu Glu Thr Leu Ala Leu Leu Glu Leu Ile Asp Asp
     50                  55                  60

Ile Gln Arg Leu Gly Leu Gly Tyr Lys Phe Arg Glu Ser Thr Ser Thr
 65                  70                  75                  80

Ser Leu Ala Met Leu Lys Met Ser Val Gly Gln Glu Ala Ser Asn Ser
                 85                  90                  95

Ser Leu His Ser Cys Ser Leu Tyr Phe Arg Leu Leu Arg Glu His Gly
            100                 105                 110

Phe Asp Ile Thr Pro Asp Val Phe Glu Lys Phe Lys Asp Glu Asn Gly
        115                 120                 125

Lys Phe Lys Asp Ser Ile Ala Lys Asp Val Arg Gly Leu Leu Ser Leu
130                 135                 140

Tyr Glu Ala Ser Phe Leu Gly Phe Glu Gly Glu Asn Ile Leu Asp Glu
145                 150                 155                 160

Ala Arg Glu Phe Thr Thr Met His Leu Asn Asn Ile Lys Asp Lys Val
                165                 170                 175

Asn Pro Arg Ile Ala Glu Glu Val Asn His Ala Leu Glu Leu Pro Leu
            180                 185                 190

His Arg Arg Val Glu Arg Leu Glu Ala Arg Arg Ile Gln Ser Tyr
        195                 200                 205

Ser Lys Ser Gly Glu Thr Asn Gln Ala Leu Leu Thr Leu Ala Lys Ile
    210                 215                 220

Asp Phe Asn Thr Val Gln Ala Val Tyr Gln Arg Asp Leu Gln Asp Val
225                 230                 235                 240

Ser Lys Trp Trp Lys Asp Thr Ala Leu Ala Asp Lys Leu Ser Phe Ala
                245                 250                 255

Arg Asp Arg Leu Met Glu Ser Phe Phe Trp Ala Ile Gly Met Ser Tyr
            260                 265                 270

Asp Pro Gln His Ser Lys Ser Arg Glu Ala Val Thr Lys Thr Phe Lys
        275                 280                 285

Leu Val Thr Val Leu Asp Asp Val Tyr Asp Val Tyr Gly Ser Leu Asp
    290                 295                 300

Glu Leu Glu Lys Phe Thr Ala Ala Glu Arg Trp Asp Val Asp Ala
305                 310                 315                 320

Ile Lys Asp Leu Pro Asp Tyr Met Lys Leu Cys Tyr Leu Ser Leu Phe
                325                 330                 335

Asn Thr Val Asn Asp Leu Ala Tyr Asp Thr Leu Lys Asp Lys Gly Glu
            340                 345                 350

Thr Val Ile Pro Ile Met Lys Lys Ala Trp Ala Asp Leu Leu Lys Ala
        355                 360                 365

Phe Leu Gln Glu Ala Gln Trp Ile Tyr Asn Lys Tyr Thr Pro Thr Phe
    370                 375                 380

Asp Glu Tyr Leu Asn Asn Ala Arg Phe Ser Val Ser Gly Cys Val Met
385                 390                 395                 400
```

```
Leu Val His Ser Tyr Phe Thr Thr Gln Asn Ile Thr Lys Glu Ala Ile
                405                 410                 415

His Ser Leu Glu Asn Tyr His Asp Leu Leu Ile Trp Pro Ser Ile Val
            420                 425                 430

Phe Arg Leu Ala Asn Asp Leu Ser Ser Lys Ala Glu Ile Glu Arg
        435                 440                 445

Gly Glu Thr Ala Asn Ser Ile Thr Cys Tyr Met Asn Glu Thr Gly Gln
        450                 455                 460

Ser Glu Glu Gln Ala Arg Glu His Ile Ser Lys Leu Ile Asp Glu Cys
465                 470                 475                 480

Phe Lys Lys Met Asn Lys Glu Met Leu Ala Thr Ser Thr Ser Pro Phe
                485                 490                 495

Glu Lys Ser Phe Ile Glu Thr Ala Ile Asn Leu Ala Arg Ile Ala Leu
                500                 505                 510

Cys Gln Tyr Gln Tyr Gly Asp Ala His Ser Asp Pro Asp Val Arg Ala
            515                 520                 525

Arg Asn Arg Ile Val Ser Val Ile Ile Asn Pro Val Glu
        530                 535                 540

<210> SEQ ID NO 2
<211> LENGTH: 20
<212> TYPE: DNA
<213> ORGANISM: Artificial Sequence
<220> FEATURE:
<223> OTHER INFORMATION: F_ibat_Nde primer

<400> SEQUENCE: 2
catatgactg cccgccgctc                                                   20

<210> SEQ ID NO 3
<211> LENGTH: 34
<212> TYPE: DNA
<213> ORGANISM: Artificial Sequence
<220> FEATURE:
<223> OTHER INFORMATION: R_ibat_Kpn primer

<400> SEQUENCE: 3
ggtaccctat tccactggat taatgataac tgac                                   34

<210> SEQ ID NO 4
<211> LENGTH: 42
<212> TYPE: DNA
<213> ORGANISM: Artificial Sequence
<220> FEATURE:
<223> OTHER INFORMATION: Ptac-IspS-F primer

<400> SEQUENCE: 4
ccatgattac gaaaggagga caatgactgc ccgccgctca gc                          42

<210> SEQ ID NO 5
<211> LENGTH: 45
<212> TYPE: DNA
<213> ORGANISM: Artificial Sequence
<220> FEATURE:
<223> OTHER INFORMATION: IspS-pawp78-R primer

<400> SEQUENCE: 5
gcatcttccc gacaactact actattccac tggattaatg ataac                       45

<210> SEQ ID NO 6
<211> LENGTH: 44
<212> TYPE: DNA
```

```
<213> ORGANISM: Artificial Sequence
<220> FEATURE:
<223> OTHER INFORMATION: Phps-IspF primer

<400> SEQUENCE: 6
gtaactatcg gagaagaaac atgactgccc gccgctcagc aaac                    44
```

METHOD FOR PRODUCING ISOPRENE USING RECOMBINANT HALOPHILIC METHANOTROPH

CROSS-REFERENCE TO RELATED APPLICATION

This application claims priority to Korean Patent Application No. 10-2016-0009372 filed Jan. 26, 2016, the disclosure of which is hereby incorporated in its entirety by reference.

The Sequence Listing associated with this application is filed in electronic format via EFS-Web and is hereby incorporated by reference into the specification in its entirety. The name of the text file containing the Sequence Listing is 1606041_ST25.txt. The size of the text file is 5,958 bytes, and the text file was created on Dec. 1, 2016.

TECHNICAL FIELD

The present invention relates to a recombinant methanotroph having an ability to produce isoprene and a method for producing isoprene using the same, and more particularly to a recombinant methanotroph in which a gene encoding an isoprene synthase having a homology of at least 70% to the amino acid sequence of *Ipomoea batatas* isoprene synthase is introduced and which has the ability to produce isoprene, and a method for producing isoprene using the recombinant methanotroph.

BACKGROUND ART

Isoprenoids are isoprene polymers that find use in pharmaceuticals, neutraceuticals, flavors, fragrances, perfume, and rubber products. Isoprene (2-methyl-1,3-butadiene) is a volatile hydrocarbon that is insoluble in water and soluble in alcohols. A commercially viable amount of isoprene can be obtained by direct isolation from petroleum C5 cracking fractions or obtained by dehydration of C5 isoalkanes or isoalkenes (Weissermel and Arpe, Industrial Organic Chemistry, 4th ed., Wiley-VCH, pp. 117-122, 2003), and the C5 skeleton can also be synthesized from smaller subunits.

Biosynthesis of isoprene occurs by two distinct metabolic pathways (Julsing et al. Appl Microbiol Biotechnol, 75:1377-1384, 2007). In eukaryotic organisms and protobionts, isoprene is synthesized through the mevalonate (MVA) pathway, whereas, in some bacteria and higher plants, isoprene is synthesized through the methylerythritol phosphate (MEP) pathway. Isoprene emission from plants is dependent on light and temperature with increases linked to leaf development. Isoprene synthase, an isoprene-producing enzyme, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been reported (Kuzma et al. Curr Microbiol, 30:97-103, 1995; Wilkins, Chemosphere, 32:1427-1434, 1996), and varies in amount with the phase of bacterial growth and the nutrient content of the culture medium (U.S. Pat. No. 5,849,970; Wagner et al. J Bacteriol, 181:4700-4703, 1999).

However, the levels of isoprene obtainable through bacterial systems of the prior art are insufficient for commercial uses. Thus, there is a need for an efficient, large scale, bacterial isoprene production process to provide feedstock for the manufacture of isoprenoids.

Meanwhile, among C1 compounds, methane gas is produced at low costs from natural gas and synthetic gas which is a mixed gas of carbon monooxide, carbon dioxide and hydrogen obtained by incinerating waste such as biomass, municipal waste, and so on. Natural gas is attracting attention as a next-generation energy source, because it abundantly exists in fossil resources and generates a relatively small amount of $CO_2$. Thus, transition from conventional petroleum to natural gas is in progress.

A methylotroph is a general name for a C1 compound assimilating microorganism that uses a carbon compound not having a C—C bond in the molecule, e.g., methane, methanol, methylamine, dimethylamine, trimethylamine or the like as a sole carbon source or energy source. Any microorganisms called methanotroph, methane-oxidizing bacteria, methanol assimilating bacteria, methanol assimilating yeast, methanol assimilating microorganism, belong to methylotrophs. Central metabolism of a methylotroph is a reaction of converting formaldehyde into an organic matter having a C—C bond after converting methanol to formaldehyde.

As methods of producing isoprene using a methanotroph, several methods that comprise externally introducing isoprene synthase were reported. However, when the foreign gene isoprene synthase is introduced into a methanotroph, there are disadvantages in that the methanotroph does not have a sufficient ability to produce isoprene, thereby isoprene production is low (US 2015-0225743; KR2015-0100666; WO2014-138419; WO2014-089436).

SUMMARY OF THE INVENTION

Accordingly, the present inventors have made extensive efforts to develop a method of producing a high yield of isoprene using, as a carbon source, methane gas or methanol which is obtained from waste such as natural gas, biomass, municipal waste or the like, and as a result, have found that, when a halophilic methanotroph constructed by transformation with an *Ipomoea batatas* isoprene synthase gene is cultured in the presence of methane or methanol, isoprene is produced in high yield, thereby completing the present invention.

It is an object of the present invention to provide a recombinant methanotroph which produces isoprene in high yield by use of methane gas or methanol as a carbon source.

Another object of the present invention is to provide a method of producing isoprene using the recombinant methanotroph.

To achieve the above object, the present invention provides a recombinant methanotroph having an ability to produce isoprene, wherein a gene encoding an isoprene synthase having a homology of at least 70% to an amino acid sequence of SEQ ID NO: 1 is introduced in the recombinant methanotroph.

The present invention also provides a method for producing isoprene, comprising the steps of: (a) culturing the recombinant methanotroph in the presence of methane or methanol as a carbon source, thereby produce isoprene; and (b) recovering the produced isoprene.

The use of a recombinant methanotroph according to the present invention enables isoprene to be produced in high yield by using, as a carbon source, methane gas or methanol which is obtained from waste such as natural gas, biomass, municipal waste or the like.

DESCRIPTION OF THE INVENTION

Figure 1:
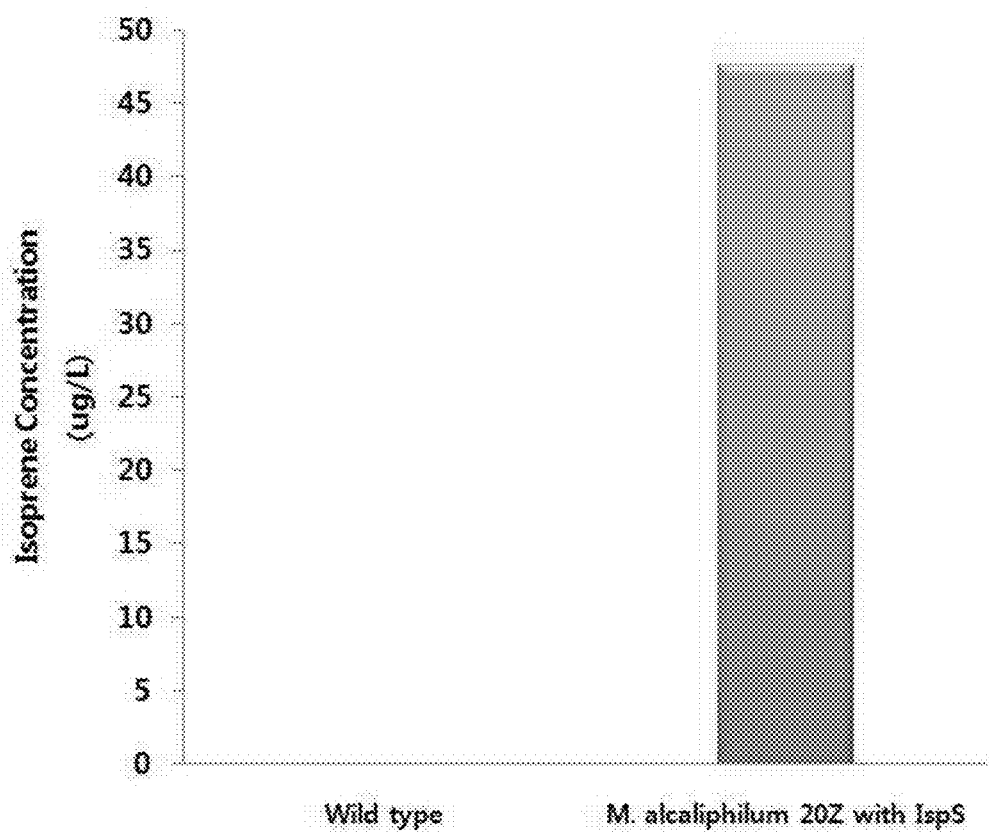
FIG. 1 shows the amount of isoprene produced by a recombinant methanotroph according to the present invention.

In the present invention, in order to produce isoprene in high yield by use of methanol or methane as a carbon source, a recombinant methanotroph was constructed by introducing an *Ipomoea batatas* isoprene synthase gene (IspS) into a halophilic methanotroph. It was found that the recombinant methanotroph exhibited the ability to produce isoprene, which did not appear in a wild-type methanotroph.

The methanotroph that is used in the present invention is a halophilic methanotroph capable of producing DMAPP through the MEP metabolic pathway by use of a carbon source as a substrate, and may contain genes encoding the following methylerythritol phosphate (MEP) pathway enzymes:

(i) MEP pathway enzymes: 1-deoxyxyluose-5-phosphate synthase (DXS), 1-deoxy-D-xyluose 5-phosphate reductoisomerase (DXR), 1-deoxy-D-ribulose 5-phosphate reductoisomerase (DRL), 4-diphophocytidyl-2C-methyl-D-erythritol synthase (ispD), 4-diphosphocytidyl-2-C-methylerythritol kinase (ispE), 2C-methyl-D-erythritol 2,4-cyclodiphosphate synthase (ispF), 1-hydroxy-2-methyl-2-(E)-butenyl 4-diphosphate synthase (ispG), isopentenyl-diphosphate: NAD(P)+oxidoreductase (ispH), and isopentyl diphosphate isomerase (IDI).

Therefore, in one aspect, the present invention is directed to a recombinant methanotroph having an ability to produce isoprene wherein a gene encoding an isoprene synthase having a homology of at least 70% to an amino acid sequence of SEQ ID NO: 1 is introduced in the recombinant methanotroph.

In the present invention, the isoprene synthase having an amino acid sequence of SEQ ID NO: 1 is an *Ipomoea batatas* isoprene synthase (IspS) showing high isoprene production efficiency.

A gene having the highest homology to the *Ipomoea batatas* IspS gene is *Olea europaea* terpene synthase 3 which merely shows a homology of 68% to the *Ipomoea batatas* IspS gene, thereby the IspS gene used in the present invention is a novel enzyme having a very low homology to a conventional terpene synthase.

In the present invention, the gene encoding an isoprene synthase may have a homology of preferably at least 70%, more preferably at least 80%, even more preferably 90%, and most preferably 95% to an amino acid sequence of SEQ ID NO: 1

In the present invention, the methanotroph may be selected from the group consisting of *Methylomonas, Methylobacter, Methylococcus, Methylosinus, Methylocystis, Methylomicrobium, Methanomonas, Methylocella,* and *Methylocapsa*. Preferably, the methanotroph that can be used in the present invention may be *Methylomicrobium alcaliphilum*, but is not limited thereto.

In an example of the present invention, the *Ipomoea batatas* IspS gene was introduced into *Methylomicrobium alcaliphilum* 20Z (DSM 19304), thereby constructing a recombinant methanotroph having an ability to biosynthesize isoprene.

In another aspect, the present invention is directed to a method for producing isoprene, comprising the steps of: (a) culturing the recombinant methanotroph in the presence of methane or methanol as a carbon source to thereby produce isoprene; and (b) recovering the produced isoprene.

The recovery of isoprene in step (b) may be performed by a known method such as gas chromatography (GC), gas chromatography-mass spectrometry (GC-MS), gas stripping, distillation, polymer membrane separation, adsorption/desorption by pervaporation, thermal desorption, vacuum desorption, solvent extraction or the like, but is not limited thereto.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Preparation of Recombinant Methanotroph by Introducing IspS Gene

To construct the plasmid BlueScript-SK-IspS, primers of F_ibat_Nde [SEQ ID NO: 2] and R_ibat_Kpn [SEQ ID NO: 3] were synthesized and the IspS gene was amplified by PCR using a pair of primers of SEQ ID NOs: 2 and 3 and inserted into a pBlueScript vector using NdeI and KpnI restriction enzymes.

Then the IspS gene was amplified from the pBlueScrip-SK-IspS using two sets of primers: Ptac-IspS-F (SEQ ID NO:4)/IspS-pawp78R(SEQ ID NO:5) and Phps-IspF (SEQ ID NO:6)/IspS-pawp78R(SEQ ID NO:5). The primers have a complementarity to Ptac or Phps or pAWP78 sequence at 5'-end (overlap region) to facilitate the annealing of fragments. All the primers used are listed in Table 1 below.

TABLE 1

Primer sequences

| SEQ ID NOS: | Names of primers | Sequences (5'->3') |
|---|---|---|
| 2 | F_ibat_Nde | CATATGACTGCCCGCCGCTC |
| 3 | R_ibat_Kpn | GGTACCCTA TTCCACTGGATTAATGATAACTGAC |
| 4 | Ptac-IspS-F | ccatgattacgaaaggaggacaATGACTGCCCGCCGCTCAGC |
| 5 | IspS-pawp78-R | GCATCTTCCCGACAACTACTACTATTCCACTGGATTAATGATAAC |
| 6 | Phps-IspF | GTAACTATCGGAGAAGAAACATGACTGCCCGCCGCTCAGCAAAC |

Ptac promoter and Phps promoter are functional synthetic hybrids derived from tac or hps promoters, respectively, and the −10 and the ribosome binding site from the hps and pmoA gene promoter, respectively.

The amplified IspS fragments were linked with the corresponding promoter region and cloned into of pAWP78 (Puri, A. W. et al., Appl Environ Microbiol. 81(5): 1775-81, 2015) using Gibson assembly (NEBuilder HiFi DNA Assembly Master Mix from NEBlabs).

The resulted fragments were transformed into NEB-5α competent E. coli. The transformed clones were cultured in LB+Kan (kanamycin) medium, and correctly assembled strains were screened by PCR. Gene constructs were obtained from 2-3 clones and sequenced to confirm it. The validated constructs (pAWP78::Ptac-ispS and pAWP78::Phps-ispS) were sub-cloned into E. coli S17-1, and incorporated into *Methylomicrobium alcaliphilum* 20Z (DSM 19304) by biparental mating (Ojala D. S. et al, Methods Enzymol. 495: 99-118, 2011). The recombinant *Methylomicrobium alcaliphilum* 20Z containing pAWP78::Ptac-ispS or pWP78::Phps-ispS were selected using a medium containing kanamycin (100 μg/mL) and Rif (50 μg/mL), which has the composition shown in Tables 2 to 5 below.

Example 2: Production of Isoprene from Recombinant Methanotroph in the Presence of Methanol Substrate To a 50-ml sterilized closed serum vial, 12.5 mL of a medium having the composition shown in Table 2 below was added, and 2 g/L of methanol as a carbon source was added. In Table 2, the compositions of a trace element solution, a phosphate solution and a carbonate solution are shown in Tables 3, 4 and 5, respectively. *Methylomicrobium alcaliphilum* 20Z transformed with the IspS gene which is constructed in Example 1, was inoculated into the medium and cultured at a temperature of 30° C. and a stirring speed of 250 rpm for 3 days.

TABLE 2

| Medium components | Contents |
|---|---|
| KNO$_3$ | 1.0 g/L |
| MgSO$_4$•7H$_2$O | 0.2 g/L |
| CaCl$_2$•2H$_2$O | 0.02 g/L |
| Trace solution (×1000) | 1 ml/L |
| NaCl | 30 g/L |
| Phosphate solution | 20 ml/L |
| Carbonate solution (1M, pH 8.8-9.0) | 40 ml/L |
| dH$_2$O | Fill up to 1 L |

TABLE 3

| Components of Trace Element Solution | Contents (g/L) |
|---|---|
| Na$_2$EDTA | 5 |
| FeSO$_4$•7H$_2$O | 2 |
| ZnSO$_4$•7H$_2$O | 0.3 |

TABLE 3-continued

| Components of Trace Element Solution | Contents (g/L) |
|---|---|
| MnCl$_2$•4H$_2$O | 0.03 |
| CoCl$_2$•6H$_2$O | 0.2 |
| CuSO$_4$•5H$_2$O | 0.3 |
| NiCl$_2$•6H$_2$O | 0.05 |
| Na$_2$MoO$_4$•2H$_2$O | 0.05 |
| H$_3$BO$_3$ | 0.03 |
| dH$_2$O | Fill up to 1 L |

TABLE 4

| Components of Phosphate Solution | Contents (g/L) |
|---|---|
| KH$_2$PO$_4$ | 5.44 |
| Na$_2$HPO$_4$ | 5.68 |

TABLE 5

| Components of Carbonate Solution | Contents (g/L) |
|---|---|
| NaHCO$_3$ | 75.6 |
| Na$_2$CO$_3$ | 10.5 |

Next, the seed culture was inoculated into a freshly prepared serum vial, and then cultured for 3 days under the same conditions as described above, after which isoprene production was analyzed.

The production of isoprene was analyzed by GC/FID (column: DB-5MS (60M length*0.25 mm I.D*0.25 mm thickness); inlet split ratio: 10:1; inlet temperature: 280° C.; oven temperature: initial 30° C. (10 min), ramp: 10° C./min, isothermal: 180° C. (0 min).

Figure 2:
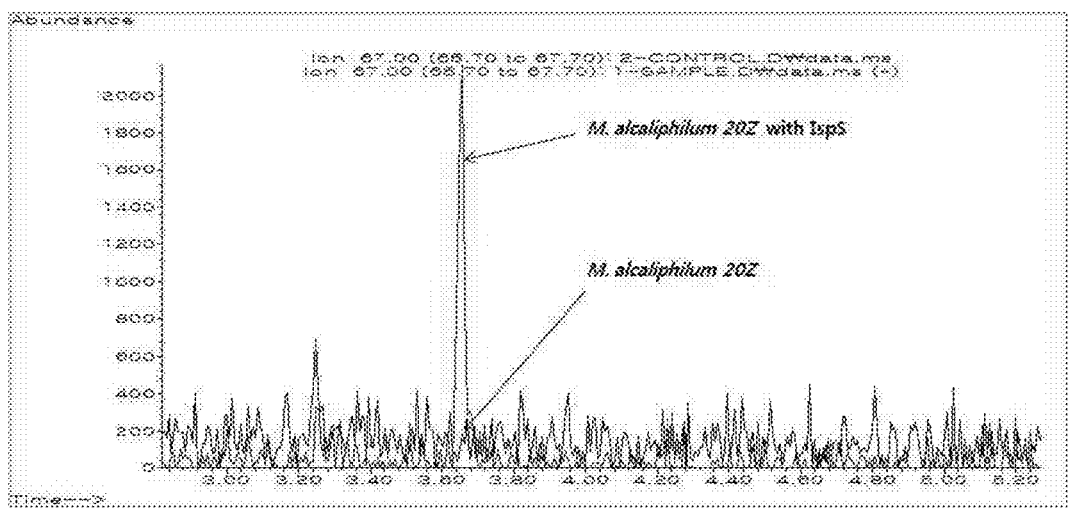
FIG. 2 shows the results of GC-MS analysis of isoprene in a culture of a recombinant methanotroph according to the present invention.

As a result, as shown in FIGS. 1 and 2, a wild-type *Methylomicrobium alcaliphilum* 20Z strain did not produce isoprene, but the strain containing the pAWP78::Ptac-ispS or pWP78::Phps-ispS, constructed in Example 1, produced isoprene at a high concentration of about 50 μg/ml.

Figure 3:
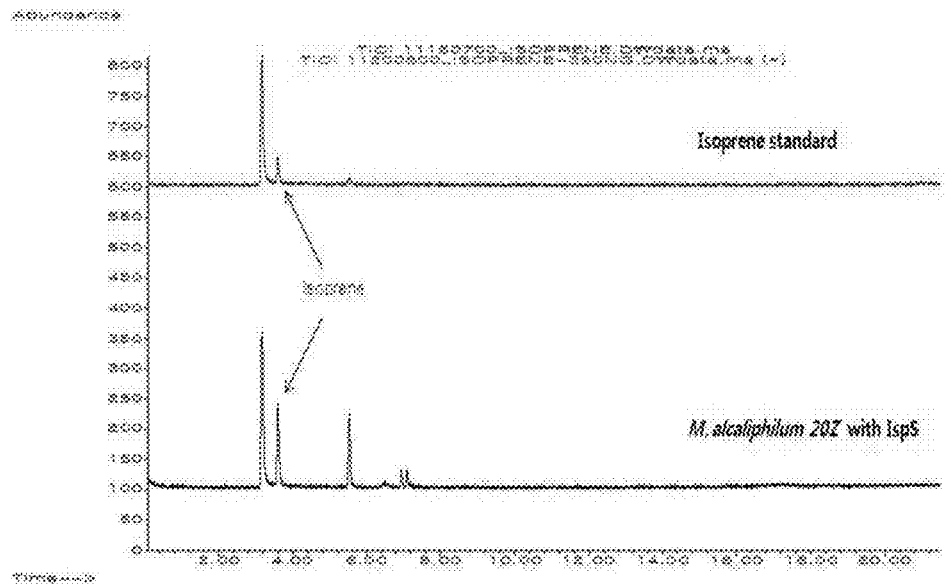
FIG. 3 shows the results of producing isoprene by a recombinant methanotroph according to the present invention in the presence of a methane substrate.

Example 3: Production of Isoprene from Recombinant Methanotroph in the Presence of Methane Substrate To a 250 ml sterilized baffled flask, 50 ml of P medium was added, and the *Methylomicrobium alcaliphilum* 20Z recombinant strain transformed with the IspS gene was inoculated into the medium and cultured at 30° C. and 200 rpm for 24 hours. As a carbon source, 2 g/L of methanol was added. Next, the cultured cells were inoculated into a 1.5-L working volume of P medium in a 3-L fermenter and cultured at 30° C., 200 rpm or higher and pH 8.7-9. As a carbon source, methane gas (10 v/v %, 90% N$_2$) was used. A mixture of the carbon source with air was injected, and isoprene was analyzed during culture of the cells. Off-gas was captured, and isoprene in the off-gas was analyzed. As a result, as shown in FIG. 3, isoprene production could be confirmed.

The invention claimed is:

1. A recombinant methanotroph having an ability to produce isoprene, into which a gene encoding an isoprene synthase having the amino acid sequence of SEQ ID NO: 1 is introduced.

2. The recombinant methanotroph of claim 1, wherein the methanotroph is selected from the group consisting of *Methylomonas, Methylobacter, Methylococcus, Methylosinus, Methylocystis, Methylomicrobium, Methanomonas, Methylocella*, and *Methylocapsa*.

3. The recombinant methanotroph of claim 2, wherein the methanotroph is *Methylomicrobium alcaliphilum*.

4. A method for producing isoprene, the method comprising the steps of:

(a) culturing the recombinant methanotroph of claim 1 in the presence of methane or methanol as a carbon source, thereby produce isoprene; and (b) recovering the produced isoprene.

5. The method of claim 4, wherein the recovery of isoprene in step (b) is performed by any one method selected from the group consisting of gas chromatography (GC), gas chromatography-mass spectrometry (GC-MS), gas stripping, distillation, polymer membrane separation, adsorption/desorption by pervaporation, thermal desorption, vacuum desorption, and solvent extraction.

* * * * *